(12) United States Patent
Mistretta et al.

(10) Patent No.: US 9,414,799 B2
(45) Date of Patent: Aug. 16, 2016

(54) SYSTEM AND METHOD FOR IMPLEMENTATION OF 4D TIME-ENERGY SUBTRACTION COMPUTED TOMOGRAPHY

(75) Inventors: Charles A. Mistretta, Madison, WI (US); Charles M. Strother, Madison, WI (US)

(73) Assignees: MISTRETTA MEDICAL, LLC, Madison, WI (US); CMS MEDICAL, LLC, Madison, WI (US)

( * ) Notice: Subject to any disclaimer, the term of this patent is extended or adjusted under 35 U.S.C. 154(b) by 0 days.

(21) Appl. No.: 13/554,772

(22) Filed: Jul. 20, 2012

(65) Prior Publication Data

US 2013/0046176 A1 Feb. 21, 2013

Related U.S. Application Data

(63) Continuation of application No. PCT/US2011/022120, filed on Jan. 21, 2011.

(60) Provisional application No. 61/297,771, filed on Jan. 24, 2010.

(51) Int. Cl.
| | | |
|---|---|---|
| *A61B 5/05* | (2006.01) | |
| *A61B 6/00* | (2006.01) | |
| *A61B 6/03* | (2006.01) | |

(Continued)

(52) U.S. Cl.
CPC ............... *A61B 6/504* (2013.01); *A61B 6/032* (2013.01); *A61B 6/405* (2013.01); *A61B 6/4014* (2013.01); *A61B 6/4035* (2013.01); *A61B 6/4441* (2013.01); *A61B 6/463* (2013.01); *A61B 6/464* (2013.01); *A61B 6/466* (2013.01); *A61B 6/481* (2013.01); *A61B 6/482* (2013.01); *A61B 6/487* (2013.01); *A61B 6/507* (2013.01); *G06T 5/50* (2013.01); *G06T 15/08* (2013.01); *A61B 6/5288* (2013.01); *A61B 6/541* (2013.01);

(Continued)

(58) Field of Classification Search
CPC .... A61B 6/032; A61B 6/4014; A61B 6/4035; A61B 6/405; A61B 6/4441; A61B 6/463; A61B 6/464; A61B 6/466; A61B 6/481; A61B 6/482; A61B 6/487; A61B 6/504; A61B 6/507; A61B 6/5288; A61B 6/541
USPC ........................................................ 600/427
See application file for complete search history.

(56) References Cited

U.S. PATENT DOCUMENTS

| | | | |
|---|---|---|---|
| 4,482,918 | A | 11/1984 | Keyes et al. |
| 6,317,621 | B1 | 11/2001 | Graumann et al. |

(Continued)

FOREIGN PATENT DOCUMENTS

WO    WO-2006/106470    10/2006

OTHER PUBLICATIONS

Chen et al., "Blood Flow Measurement by Cone-Beam CT Bolus Imaging", Proceedings of the SPIE, vol. 6143, 61432J, 2006, 12 pages.

(Continued)

*Primary Examiner* — Jonathan Cwern
*Assistant Examiner* — Amelie R Gillman
(74) *Attorney, Agent, or Firm* — Foley & Lardner LLP

(57) ABSTRACT

A method is disclosed for generating a time resolved series of time and energy subtracted 3D volume reconstructions, e.g., using a switched dual energy C-Arm type X-ray imaging system or a bi-plane type X-ray imaging system.

11 Claims, 13 Drawing Sheets

(51) Int. Cl.
  *G06T 5/50* (2006.01)
  *G06T 15/08* (2011.01)
(52) U.S. Cl.
  CPC ............... *G06T2207/10081* (2013.01); *G06T 2207/30101* (2013.01)

(56) References Cited

U.S. PATENT DOCUMENTS

| | | | |
|---|---|---|---|
| 6,823,204 B2 | 11/2004 | Grass et al. | |
| 6,983,182 B2 | 1/2006 | Mistretta | |
| 7,020,314 B1 | 3/2006 | Suri et al. | |
| 7,054,405 B2 | 5/2006 | Edic et al. | |
| 7,305,062 B2 | 12/2007 | Hambuchen et al. | |
| 7,545,901 B2 | 6/2009 | Mistretta | |
| 7,590,442 B2 | 9/2009 | Boese et al. | |
| 7,738,626 B2 | 6/2010 | Weese et al. | |
| 7,839,403 B2 | 11/2010 | Heigl et al. | |
| 8,009,885 B2 | 8/2011 | Grass et al. | |
| 8,285,360 B2 | 10/2012 | Kabasawa | |
| 8,643,642 B2* | 2/2014 | Mistretta | A61B 6/4441 345/419 |
| 8,654,119 B2* | 2/2014 | Mistretta | A61B 6/02 345/419 |
| 2001/0007593 A1* | 7/2001 | Oosawa | 382/132 |
| 2004/0022359 A1* | 2/2004 | Acharya et al. | 378/98.11 |
| 2004/0116812 A1 | 6/2004 | Selzer et al. | |
| 2004/0247070 A1 | 12/2004 | Ali et al. | |
| 2005/0080328 A1 | 4/2005 | Vass et al. | |
| 2005/0084060 A1 | 4/2005 | Seppi et al. | |
| 2005/0232389 A1 | 10/2005 | Klingenbeck-Regn | |
| 2005/0245896 A1 | 11/2005 | Kucharczyk et al. | |
| 2006/0122492 A1 | 6/2006 | Kucharczyk et al. | |
| 2006/0165213 A1* | 7/2006 | Hambuchen et al. | 378/9 |
| 2006/0173297 A1 | 8/2006 | Popescu | |
| 2006/0250386 A1 | 11/2006 | Movassaghi et al. | |
| 2007/0009080 A1 | 1/2007 | Mistretta | |
| 2007/0021669 A1 | 1/2007 | Miga et al. | |
| 2007/0055148 A1 | 3/2007 | Klingenbeck-Regn | |
| 2007/0058781 A1 | 3/2007 | Nakano et al. | |
| 2007/0165936 A1 | 7/2007 | Yonezawa et al. | |
| 2007/0183569 A1 | 8/2007 | Boese et al. | |
| 2008/0051648 A1 | 2/2008 | Suri et al. | |
| 2008/0192997 A1 | 8/2008 | Grass et al. | |
| 2008/0212857 A1 | 9/2008 | Pfister et al. | |
| 2008/0243435 A1 | 10/2008 | Deinzer et al. | |
| 2008/0300478 A1 | 12/2008 | Zuhars et al. | |
| 2008/0304728 A1* | 12/2008 | Licato et al. | 382/131 |
| 2009/0010380 A1* | 1/2009 | Gotoh | 378/5 |
| 2009/0074277 A1 | 3/2009 | Deinzer et al. | |
| 2009/0088830 A1 | 4/2009 | Mohamed et al. | |
| 2009/0093712 A1 | 4/2009 | Busch et al. | |
| 2009/0097611 A1* | 4/2009 | Nishide et al. | 378/5 |
| 2009/0097721 A1 | 4/2009 | Kingsbury et al. | |
| 2009/0198126 A1 | 8/2009 | Klingenbeck-Regn | |
| 2009/0244300 A1 | 10/2009 | Levin et al. | |
| 2009/0274358 A1* | 11/2009 | Flohr et al. | 382/131 |
| 2010/0034446 A1 | 2/2010 | Zhu et al. | |
| 2010/0053209 A1 | 3/2010 | Rauch et al. | |
| 2010/0061611 A1 | 3/2010 | Xu et al. | |
| 2010/0081917 A1 | 4/2010 | Zhang et al. | |
| 2010/0158341 A1 | 6/2010 | Baumgart | |
| 2010/0201786 A1 | 8/2010 | Schaefer et al. | |
| 2010/0296623 A1 | 11/2010 | Mielekamp et al. | |
| 2011/0037761 A1 | 2/2011 | Mistretta et al. | |
| 2011/0038517 A1 | 2/2011 | Mistretta et al. | |
| 2013/0039559 A1 | 2/2013 | Grass et al. | |
| 2013/0123611 A1 | 5/2013 | Riederer et al. | |

OTHER PUBLICATIONS

International Search Report and Written Opinion for PCT Application No. PCT/US2010/045637, mail date Apr. 12, 2011, 7 pages.

International Search Report and Written Opinion for PCT Application No. PCT/US2011/022120, mail date Aug. 26, 2011, 9 pages.

Kohler et al., "Method for Flow Reconstruction from Dynamic X-Ray Projection Measurements", Nuclear Science Symposium Conference Record, 2004 IEEE, vol. 5, Oct. 2004, 4 pages.

Lessard et al., "Automatically Driven Vector for Line Segmentation in 2D and Biplane Imaging Modality", 15 International Conference of Image Analysis and Processing, Italy, Sep. 8-11, 2009, 9 pages.

Liu et al., "Renal Perfusion and Hemodynamics: Accurate in Vivo Determination at CT with a 10-Fold Decrease in Radiation Dose and HYPR Noise Reduction", Radiology, vol. 253, No. 1, Oct. 2009, 8 pages.

Mistretta et al., "HYPR: Constrained Reconstruction for Enhanced SNR in Dynamic Medical Imaging", Medical Imaging 2008: Physics of Medical Imaging, Proceedings of the SPIE, vol. 6913, 2008, 9 pages.

Nth Root, http://www.mathisfun.com/numbers/nth-root.html, Archived on Dec. 21, 2007, Retrieved Jul. 10, 2012 from http://web.archive.org/web/20071221121146/http://www.mathisfun.com/numbers/nth-root.html, 6 pages.

Pollmann et al., "Four Dimensional Intravenous Cone-Beam Computed Tomographic Subtraction Angiography", Investigative Radiology, vol. 43, No. 11, Nov. 2008, 9 pages.

Schmitt et al., "An X-Ray-Based Method for the Determination of the Contrast Agent Propagation in 3-D Vessel Structures", IEEE Transactions on Medical Imaging, vol. 21, No. 3, Mar. 2002, 12 pages.

Schmitt et al., "Reconstruction of Blood Propagation in Three-Dimensional Rotational X-ray Angiography (3D-RA)", Computerized Medical Imaging and Graphics, vol. 29, Issue 7, Oct. 2005, 14 pages.

Waechter et al., "Using Flow Information to Support 3D Vessel Reconstruction from Rotational Angiography", Med. Phys. 35 (7), Jul. 2008, 15 pages.

International Search Report and Written Opinion for PCT Application No. PCT/US2012/042491, mailed Mar. 4, 2013, 10 pages.

Dumay et al. "Developments towards slice-wise three-dimensional reconstruction of the distribution of the contrast perfusion in the myocardial muscle from biplane angiographic view." International Journal of Cardiac Imaging 5, 1990, pp. 213-224.

Hamarneh et al., "Automatic Line Detection", Project Report for the Computer Vision Course Lund, Simon Fraser University, Sep. 1999, 29 pages.

Love et al., "An Empirical Study of Block Matching Techniques for the Detection of Moving Objects", Center for Applied Scientific Computing, Lawrence Livermore National Laboratory, Jan. 9, 2006, 38 pages.

Mistretta et al., "Highly Constrained Backprojection for Time-Resolved MRI", Magnetic Resonance in Medicine, vol. 55, Dec. 9, 2005, pp. 30-40.

Mistretta, Charles A., "Sub-Nyquist Acquisition and Constrained Reconstruction in Time Resolved Angiography", Medical Physics, AIP, vol. 38, No. 6, May 27, 2011, pp. 2399-2403.

Zeng et al., "Estimating 3D Respiratory Motion from Orbiting Views", 2005 IEEE Nuclear Science Symposium Conference Record, Oct. 23, 2005, pp. 2399-2403.

Zhang et al., "Estimating Continuous 4D Wall Motion of Cerebral Aneurysm from 3D Rotational Angiography", MICCAI, Sep. 20, 2009, pp. 140-147.

Zhang et al., "Morphodynamic Analysis of Cerebral Aneurysm Pulsation From Time-Resolved Rotational Angiography", IEEE Transactions on Medical Imaging, vol. 28, No. 7, Jul. 1, 2009, pp. 1105-1116.

\* cited by examiner

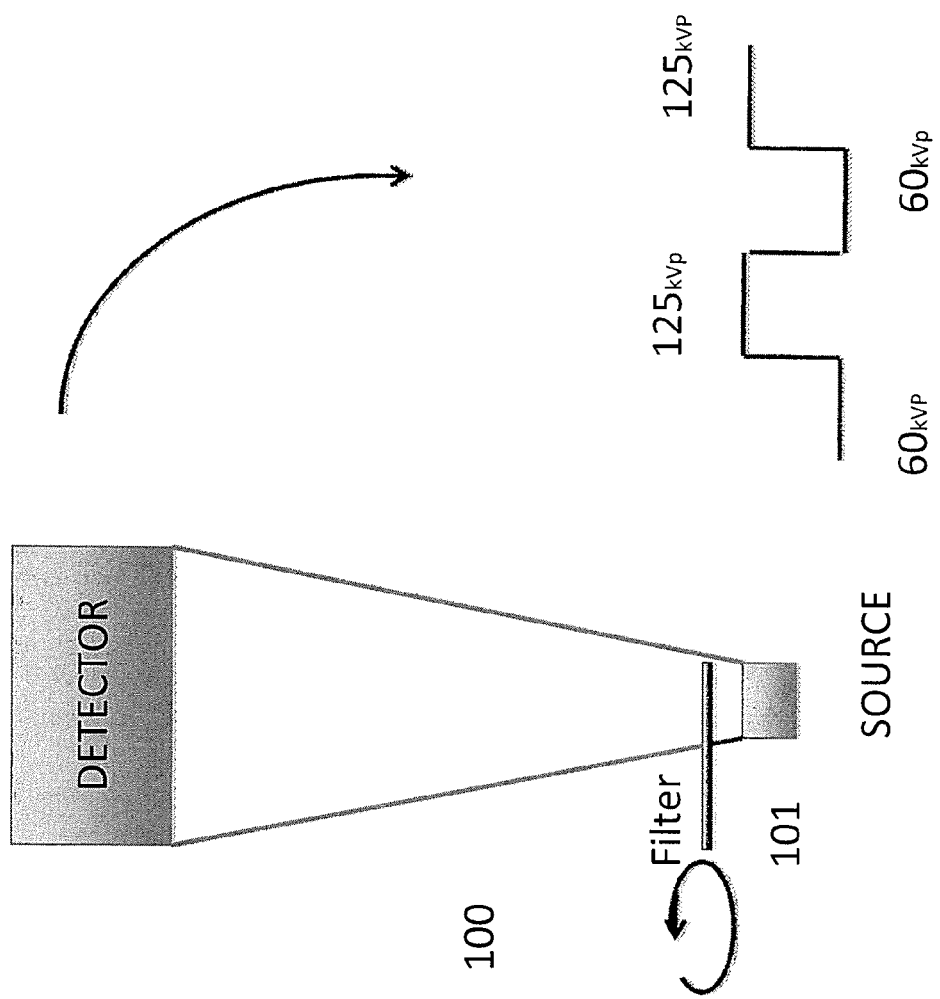

SYSTEM AND METHOD FOR IMPLEMENTATION OF 4D TIME-ENERGY SUBTRACTION COMPUTED TOMOGRAPHY

CROSS-REFERENCE TO RELATED APPLICATIONS

This application is a continuation of International PCT Application No. PCT/US2011/022120, filed Jan. 21, 2011, which in turn claims benefit of U.S. Provisional Patent Application No. 61/297,771 titled SYSTEM AND METHOD FOR IMPLEMENTATION OF 4D TIME-ENERGY SUBTRACTION COMPUTED TOMOGRAPHY filed Jan. 24, 2010, the entire contents of each of the forgoing applications are hereby incorporated by reference in their entirety herein.

FIELD

The present disclosure relates to medical imaging and related devices and techniques, such as digital subtraction angiography.

BACKGROUND

X-Ray Computed Tomography (CT) was introduced in the late 1970s as a means for forming three dimensional images of human anatomy. Although its initial spatial resolution was inferior to that of film radiography, it brought a new level of contrast resolution that enabled radiologists to discern previously undetectable low contrast pathology. The apparatus configuration evolved through many generations and is often configured using a rotating X-ray source which is opposed by a detector array rotating in fixed relationship to the source. The x-ray source is often mounted on a C-arm system or conventional gantry. The detector arrays often consist of two dimensional arrays of discrete detectors in conventional CT or in the form of a large area cone beam flat panel detector in C-Arm CT.

Conventional CT is used for a wide range of diagnostic tasks and generally rather scatter free signal detection due to the smaller area of the detector arrays, although these areas are increasing in recent years. C-Arm CT is typically used for interventional procedures where it has been recently possible to obtain 3D Digital Subtraction Angiographic (DSA) data reconstructions by performing a CT angiogram following the introduction of contrast (e.g., iodine contrast) into the vascular system. CT angiography can also be implemented on conventional CT systems but due to the small detector area, the injected contrast bolus must be followed and the timing of the gantry or table advanced relative to the bolus traversal, which can pose timing problems that result in images being obtained during suboptimal opacification.

In the 1980's the concept of spiral CT was introduced. In this mode, rather than obtaining one slice at a time, the table is advanced through the rotating gantry and the x-rays passed through the patient in a helical fashion. Using data interpolation, reconstruction of a series of CT images of sequential planes can be quickly obtained.

Imaging enhancement procedures have long been used to generate better quality and more useful medical subject images, e.g., for use in X-ray CT applications. One such method was described in an article titled, The Use of a General Description of the Radiological Transmission Image, *Optical Engineering* 13(2):134; 1974., hereby incorporated by reference in it's entirety. The following Taylor expansion was presented relating the value of a radiological transmission image at two points in the multi-variable space defined by coordinates, x, y, and z, radiation energy E and time t:

Equation 1
$$I(x', y', z', E', t) = I(x, y, z, E, t) = \frac{dI}{dx}\Delta x + \frac{dI}{dy}\Delta y + \frac{dI}{dz}\Delta z + \frac{dI}{dt}\Delta t +$$
$$\frac{dI}{dE}\Delta E + \frac{d^2 I}{dEdz}\Delta E\Delta z + \frac{d^2 I}{dEdt}\Delta E\Delta t + \frac{d^3 I}{dEdtdz}\Delta E\Delta t\Delta z$$

where the two points in variable space are related by $$(x',y',z',E',t')=(x+\Delta x, y+\Delta y, z+\Delta z, E+\Delta E, t+\Delta t).$$

Information corresponding to the various terms in the expansion may be accessed using suitable image subtraction techniques. For example, time subtraction (i.e., subtraction of images acquired at differing times) may be used to access information regarding the fifth term (including the time derivative) in the expansion of Equation 1.

SUMMARY

The inventors have realized that time and energy image subtraction techniques, as described herein, may advantageously provide medical images with a high level of detail and a high level of material selectivity. Equation 1 designates the generic terms that might lead to medical images in terms of available variables. Conventional medical imaging technologies may not allow for implementation of all these terms. For example, in image subtraction techniques performed at a fixed radiation energy, terms including $\Delta E$ will not be implemented.

Techniques described herein apply multi-energy imaging (i.e., allowing subtraction of images acquired at two or more radiation energy levels) and multi-energy and multi-time imaging to access higher order terms such as the dual energy/time and z derivative term. The first order spatial derivative terms are associated with image enhancement procedures such as spatial filtering as performed on single two dimensional images taken at a single energy and time.

The first order term in the depth variable z can be associated with tomographic imaging such as computed tomography (CT). Images of this type display information as individual slices in a patient. The first order time derivative term can be identified with multiple time subtraction techniques, such as film subtraction or digital subtraction angiography. The first order energy derivative term is the one that may be isolated using energy imaging and can be used to select various material components in the imaged region such as soft tissue, bone or contrast material. The second order term in depth and energy represents dual energy tomography.

The second order term in time and energy can be thought of as the time subtraction of two energy subtraction images. Such a subtraction may be advantageous, because, in many contrast based applications, bone material may be identified that does not mis-register in pre- and post-contrast images and that will be subtracted by the time subtraction operation. A comparison of standard (time subtracted only) DSA image and the hybrid time-energy subtracted DSA is shown in FIG. 7. Note the improved image quality for the hybrid subtraction. In some applications motion, e.g., swallowing or bowel peristalsis can cause soft tissue mis-registration. Techniques described herein may reduce or eliminate the problems identified above by performing a time subtraction of two tissue subtracted images (e.g., acquired using dual energy techniques).

In some cases, second order time and energy subtraction techniques experience disadvantageous levels of noise associated with the second order subtraction technique. Techniques described herein reduce or overcome this disadvantage by implementation of the third order term in depth, energy and time from Equation 1, which corresponds to a CT version of hybrid time and energy subtraction.

For example, as described in detail below, various embodiments are designed and are applied for the generation of a time resolved, energy subtracted set of 3D image volumes that exhibit advantageously low sensitivity to tissue motion. The techniques may be used in conjunction with time resolved, three dimensional ("4D") DSA techniques using time-separated dual energy exposures so that applications in the heart and abdomen can be pursued with decreased artifacts due to tissue motion.

In one aspect, a method is disclosed including: obtaining a non-contrast low energy time resolved series of image projections of a region of interest in a subject taken at a first energy level in the absence of a contrast agent; obtaining a non-contrast high energy time resolved series of image projections of a region of interest in a subject taken at a second energy level higher than the first energy level in the absence of a contrast agent ; obtaining a contrast low energy time resolved series of image projections of a region of interest in a subject taken at the first energy level in the presence of a contrast agent; obtaining a contrast high energy time resolved series of image projections of a region of interest in a subject taken at the second energy level in the presence of a contrast agent; generating a time resolved series of non-contrast energy subtracted image projections based on the non-contrast low energy time resolved series and high energy time resolved series; generating a time resolved series of contrast energy subtracted image projections based on the contrast low energy time resolved series and high energy time resolved series; generating a time independent non-contrast low energy three dimensional volume based on the non-contrast low energy time resolved series; generating a time independent non-contrast high energy three dimensional volume based on the non-contrast high energy time resolved series; generating a time independent contrast low energy three dimensional volume based on the contrast low energy time resolved series; and generating a time independent contrast high energy three dimensional volume based on the contrast high energy time resolved series.

Some embodiments include: generating a time independent non-contrast energy subtracted three dimensional volume based on the time independent non-contrast high energy three dimensional volume and low energy three dimensional volume; and generating a time independent contrast energy subtracted three dimensional volume based on the time independent contrast high energy three dimensional volume and low energy three dimensional volume.

Some embodiments include: generating a time resolved energy and time subtracted series of projections based on the time resolved series of non-contrast subtracted image projections and the time resolved series of contrast subtracted image projections.

Some embodiments include generating a time independent time and energy subtracted three dimensional volume based on the time independent contrast energy subtracted three dimensional volume and non-contrast energy subtracted three dimensional volume.

Some embodiments include generating a time resolved series of energy and time subtracted three dimensional volumes based on the time resolved energy and time subtracted series of projections and the time independent time and energy subtracted three dimensional volume.

In some embodiments, the time resolved energy and time subtracted series of projections includes material selective projections.

In some embodiments, the time independent time and energy subtracted three dimensional volume includes a material selective volume.

In some embodiments, the time resolved series of energy and time subtracted three dimensional volumes includes a material and contrast selective volume.

In some embodiments, the time resolved series of energy and time subtracted three dimensional volumes includes a time resolved series of digital subtraction angiography volumes.

Some embodiments include displaying at least one image of the subject based on the time resolved series of energy and time subtracted three dimensional volumes. In some embodiments, the at least one image is a parametric image.

Some embodiments include obtaining corresponding high energy and low energy image projections sequentially. Some embodiments include providing a radiation source and detector; and sequentially varying the energy level of the radiation source to obtain the corresponding high energy and low energy image projections. Some embodiments include varying a filtration of the radiation source based on the energy level of the source.

Some embodiments include obtaining corresponding high energy and low energy image projections substantially simultaneously. Some embodiments include: providing a first radiation source and a first detector; providing a second radiation source and a second detector; In some embodiments, obtaining corresponding high energy and low energy image projections substantially simultaneously includes: obtaining a first image projection at the first energy level with the first source and first detector; and obtaining the second image projection at the second energy level with the second source and second detector.

Some embodiments include a first filter for the first source and a second filter for the second source.

In some embodiments, at least one series of image projections includes angularly displaced projections.

In some embodiments, the first energy level is less than 80 kVp and the second energy level is greater than 80 kVp. In some embodiments, the first energy level is in the range of 50 kVp to 80 kVp. In some embodiments, the second energy level is greater than 100 kVp.

In some embodiments, at least one series of image projections is obtained using a rotating C-arm X-ray device. In some embodiments, at least two series of image projections taken at differing energy levels are substantially simultaneously obtained using a rotating bi-plane X-ray device.

In some embodiments, at least one series of image projections is obtained using prospective cardiac gating. In some embodiments, at least one series of image projections is obtained using retrospective cardiac gating.

In another aspect, an apparatus is disclosed including: a processor configured to: obtain a non-contrast low energy time resolved series of image projections of a region of interest in a subject taken at a first energy level in the absence of a contrast agent; obtain a non-contrast high energy time resolved series of image projections of a region of interest in a subject taken at a second energy level higher than the first energy level in the absence of a contrast agent; obtain a contrast low energy time resolved series of image projections of a region of interest in a subject taken at the first energy level in the presence of a contrast agent; obtain a contrast high energy time resolved series of image projections of a region of interest in a subject taken at the second energy level in the presence of a contrast agent; generate a time resolved series of non-contrast energy subtracted image projections based on the non-contrast low energy time resolved series and high energy time resolved series; generate a time resolved series of contrast energy subtracted image projections based on the contrast low energy time resolved series and high energy time resolved series; generate a time independent non-contrast low energy three dimensional volume based on the non-contrast low energy time resolved series; generate a time independent non-contrast high energy three dimensional volume based on the non-contrast high energy time resolved series; generate a time independent contrast low energy three dimensional volume based on the contrast low energy time resolved series; and generate a time independent contrast high energy three dimensional volume based on the contrast high energy time resolved series.

In some embodiments, the processor is further configured to: generate a time independent non-contrast energy subtracted three dimensional volume based on the time independent non-contrast high energy three dimensional volume and low energy three dimensional volume; and generate a time independent contrast energy subtracted three dimensional volume based on the time independent contrast high energy three dimensional volume and low energy three dimensional volume.

In some embodiments, the processor is further configured to: generating a time resolved energy and time subtracted series of projections based on the time resolved series of non-contrast subtracted image projections and the time resolved series of non-contrast subtracted image projections.

In some embodiments, the processor is further configured to: generate a time independent time and energy subtracted three dimensional volume based on the time independent contrast energy subtracted three dimensional volume and the-contrast energy subtracted three dimensional volume.

In some embodiments, the processor is further configured to: generate a time resolved series of energy and time subtracted three dimensional volumes based on the time resolved energy and time subtracted series of projections and the time independent time and energy subtracted three dimensional volume.

In some embodiments, the time resolved energy and time subtracted series of projections includes material selective projections. In some embodiments, the time independent time and energy subtracted three dimensional volume includes a material selective volume. In some embodiments, the time resolved series of energy and time subtracted three dimensional volumes includes a material and contrast selective volume.

In some embodiments, the time resolved series of energy and time subtracted three dimensional volumes includes a time resolved series of digital subtraction angiography volumes.

Some embodiments include a display in communication with the processor and configured to display at least one image of the subject based on the time resolved series of energy and time subtracted three dimensional volumes. In some embodiments, the at least one image is a parametric image.

Some embodiments include an imaging device in communication with the processor and configured to obtain corresponding high energy and low energy image projections sequentially.

In some embodiments, the imaging device includes a radiation source and a corresponding detector, and is configured to: sequentially vary the energy level of the radiation source to obtain the corresponding high energy and low energy image projections.

In some embodiments, the imaging device includes a filter configured to vary filtration of the radiation source based on the energy level of the source.

Some embodiments including an imaging device in communication with the processor and configured to obtain corresponding high energy and low energy image projections substantially simultaneously. In some embodiments, the imaging device includes: a first radiation source and a first detector; and a second radiation source and a second detector. The imaging device is configured to obtain corresponding high energy and low energy image projections substantially simultaneously by: obtaining a first image projection at the first energy level with the first source and first detector; and obtaining the second image projection at the second energy level with the second source and second detector. Some embodiments include a first filter for the first source and a second filter for the second source.

In some embodiments, at least one series of image projections includes angularly displaced projections.

In some embodiments, the first energy level is less than 80 kVp and the second energy level is greater than 80 kVp. In some embodiments, the first energy level is in the range of 50 kVp to 80 kVp. In some embodiments, the second energy level is greater than 100 kVp.

Some embodiments include a rotating C-arm X-ray device in communication with the processor and configured to obtain least one series of image projections.

Some embodiments include a rotating bi-plane X-ray device configured to substantially simultaneously obtain at least two series of image projections taken at differing energy levels.

In some embodiments, the processor includes at least one input for receiving electrocardiogram information related to the subject. In some embodiments, the processor is configured to obtain at least one series of image projections using prospective or retrospective cardiac gating.

Various embodiments may include any of the above described elements, steps, techniques, etc, either alone or in any suitable combination.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing.

FIG. 2 illustrates an implementation of an imaging technique using a single C-arm system incorporating rapid energy switching;

DETAILED DESCRIPTION

Figure 1A:
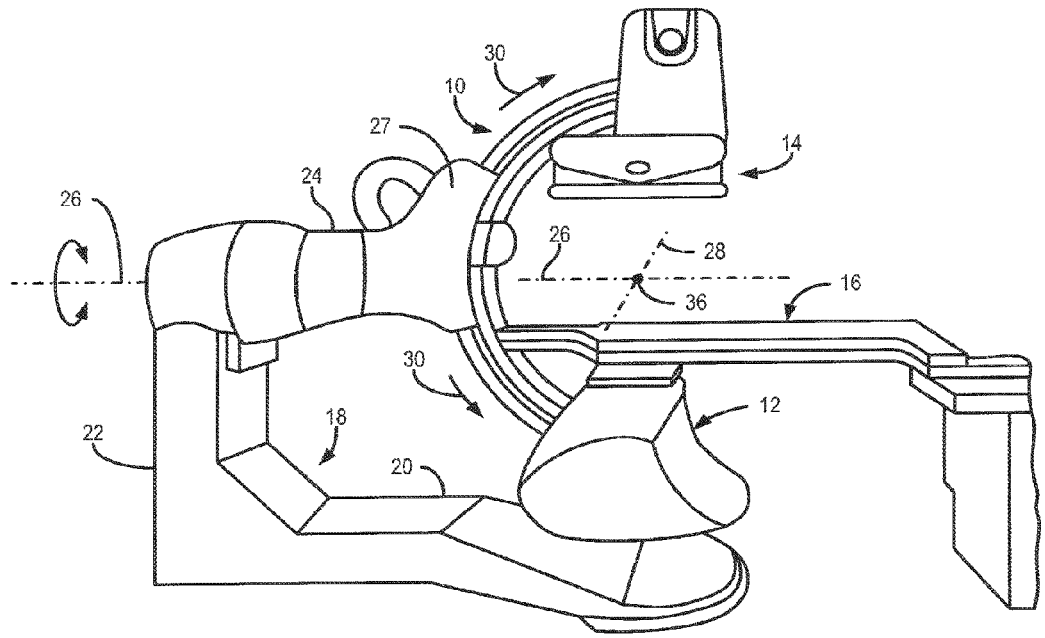
FIGS. 1A and 1B depict a rotational x-ray system configured to carry out a process.

Referring to FIG. 1A, a rotational x-ray system is illustrated for use in connection with interventional procedures. It is characterized by a gantry having a C-arm 10 which carries an x-ray source assembly 12 on one of its ends and an x-ray detector array assembly 14 at its other end. The gantry enables the x-ray source 12 and detector 14 to be oriented in different positions and angles around a patient disposed on a table 16, while enabling a physician access to the patient.

The gantry includes an L-shaped pedestal 18 which has a horizontal leg 20 that extends beneath the table 16 and a vertical leg 22 that extends upward at the end of the horizontal leg 20 that is spaced from the table 16. A support arm 24 is rotatably fastened to the upper end of vertical leg 22 for rotation about a horizontal pivot axis 26. The pivot axis 26 is aligned with the centerline of the table 16 and the arm 24 extends radially outward from the pivot axis 26 to support a C-arm drive assembly 27 on its outer end. The C-arm 10 is slidably fastened to the drive assembly 27 and is coupled to a drive motor (not shown) which slides the C-arm 10 to revolve it about a C-axis 28 as indicated by arrows 30. The pivot axis 26 and C-axis 28 intersect each other at an isocenter 36 located above the table 16 and they are perpendicular to each other.

The x-ray source assembly 12 is mounted to one end of the C-arm 10 and the detector array assembly 14 is mounted to its other end. The x-ray source 12 emits a beam of x-rays which are directed at the detector array 14. Both assemblies 12 and 14 extend radially inward to the pivot axis 26 such that the center ray of this beam passes through the system isocenter 36. The center ray of the beam can thus be rotated about the system isocenter around either the pivot axis 26 or the C-axis 28, or both during the acquisition of x-ray attenuation data from a subject placed on the table 16.

The x-ray source assembly 12 contains an x-ray source which emits a beam of x-rays when energized. The center ray passes through the system isocenter 36 and impinges on a two-dimensional flat panel digital detector housed in the detector assembly 14. The detector 38 is a multi element (e.g., 2048 by 2048) two-dimensional array of detector elements having a size of 41 cm by 41 cm (or any other suitable dimension). Each element produces an electrical signal that represents the intensity of an impinging x-ray and hence the attenuation of the x-ray as it passes through the patient. During a scan the x-ray source assembly 12 and detector array assembly 14 are rotated about the system isocenter 36 to acquire x-ray attenuation projection data from different angles. The detector array is able to acquire a given number of projections, or views, per second and, in some embodiments, this is the limiting factor that determines how many views can be acquired for a prescribed scan path and speed. In some embodiments, the detector array is able to acquire at least about 10 scans per minute, about 20 scans per minute, about 30 scans per minute, about 50 scans per minute, or more, e.g., in the range of 10-30 scans per minute.

Figure 1B:
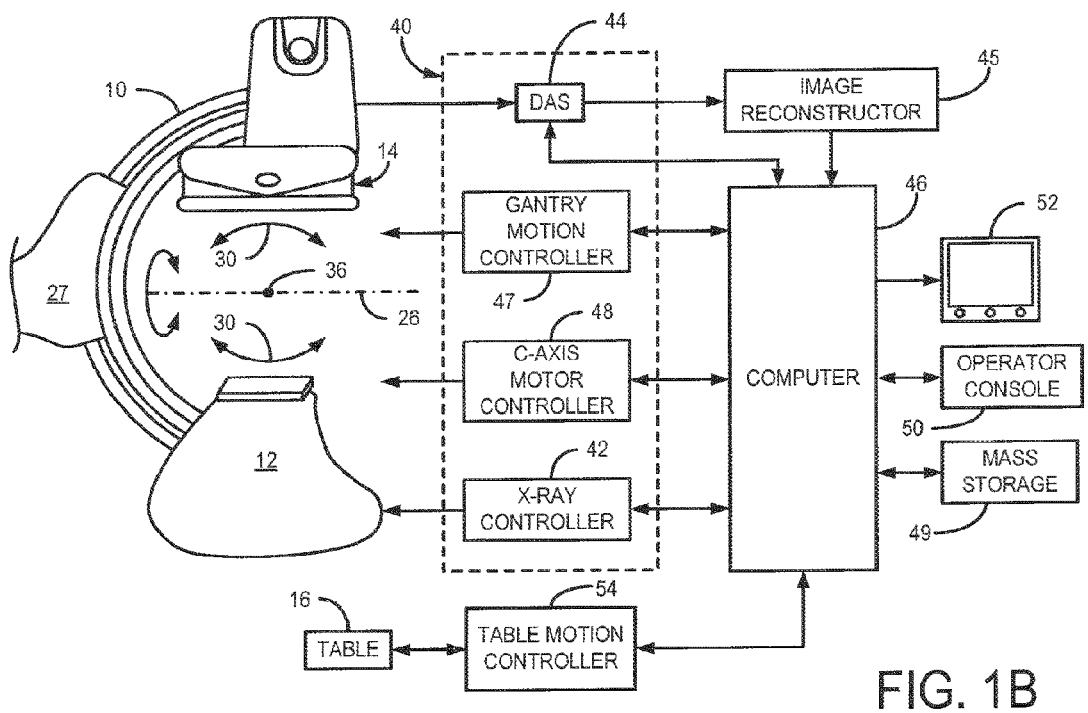

Referring particularly to FIG. 1B, the rotation of the assemblies 12 and 14 and the operation of the x-ray source are governed by a control mechanism 40 of the x-ray system. The control mechanism 40 includes an x-ray controller 42 that provides power and timing signals to the x-ray source assembly 12. A data acquisition system (DAS) 44 in the control mechanism 40 samples data from detector elements 38 and passes the data to an image reconstructor 45. The image reconstructor 45, receives digitized x-ray data from the DAS 44 and performs high speed image reconstruction according to the methods of the present invention. The reconstructed image is applied as an input to a computer 46 which stores the image in a mass storage device 49 or processes the image further to produce parametric images according to the teachings of the present invention. It is contemplated that the computer 46 may be or include components of a digital vascular image processor (DVIP) system, e.g., of any suitable type known in the art.

The control mechanism 40 also includes gantry motor controller 47 and a C-axis motor controller 48. In response to motion commands from the computer 46 the motor controllers 47 and 48 provide power to motors in the x-ray system that produce the rotations about respective pivot axis 26 and C-axis 28. As will be discussed below, a program executed by the computer 46 generates motion commands to the motor drives 47 and 48 to move the assemblies 12 and 14 in a prescribed scan path.

The computer 46 also receives commands and scanning parameters from an operator via console 50 that has a keyboard and other manually operable controls. An associated cathode ray tube display 52 allows the operator to observe the reconstructed image and other data from the computer 46. The operator supplied commands are used by the computer 46 under the direction of stored programs to provide control signals and information to the DAS 44, the x-ray controller 42 and the motor controllers 47 and 48. In addition, computer 46 operates a table motor controller 54 which controls the motorized table 16 to position the patient with respect to the system isocenter 36.

Whereas conventional reconstruction methods generally necessitate the acquisition of a minimum number of projections dictated by the Nyquist theorem, some embodiments of the devices and techniques of the present disclosure impart temporal resolution from a time-series of 2D images into time independent 3D image volume or volumes to create time-resolved 3D medical images. This allows, among other things, the production of 3D angiograms with both exquisite detail and high temporal resolution. The method can be implemented using a wide-variety of medical imaging systems, such as CT systems, fluoroscopy systems, and the above-discussed rotational x-ray system, either alone or in combination. Accordingly, the present description first presents a generalized method for producing time-resolved 3D images before proceeding to more specific implementations and extensions of the method.

According to at least one embodiment, implementation of the energy and time subtraction tomographic method includes data taken at two different times (e.g., at a time before and a time after contrast injection into an imaging subject) and at two different imaging beam energies. Thus, in some embodiments, the imaging process requires four separable acquisitions, but just one contrast injection.

In some embodiments, these four acquisitions may be obtained in an efficient manner using a C-Arm system with a variable energy beam source. For example, FIG. 2 shows a single source/detector C-arm system 100 (e.g., of the type shown in FIGS. 1A and 1B) featuring a source that has the ability to rapidly switch between the two chosen energies 102 (as shown, 60 and 125 kVp) during the C-arm rotational acquisition. For example, in some embodiments, the source may include an X-ray tube whose operating power level may be modulated, e.g., as controlled by the computer 46 of the imaging system. In some embodiments, the energy level may be modulated using one or more filters or attenuators moved in and out of the beam. In other embodiments, the beam energy may be modulated using any other suitable technique known in the art.

With this system two sweeps may be necessary, one before contrast injection and one after contrast injection. During the energy switching process a rotating filter wheel 101 may optionally be placed in front of the x-ray beam so that more filtration can be used for the high-energy exposure. Sequential projections are acquired at alternating energies.

Figure 3:
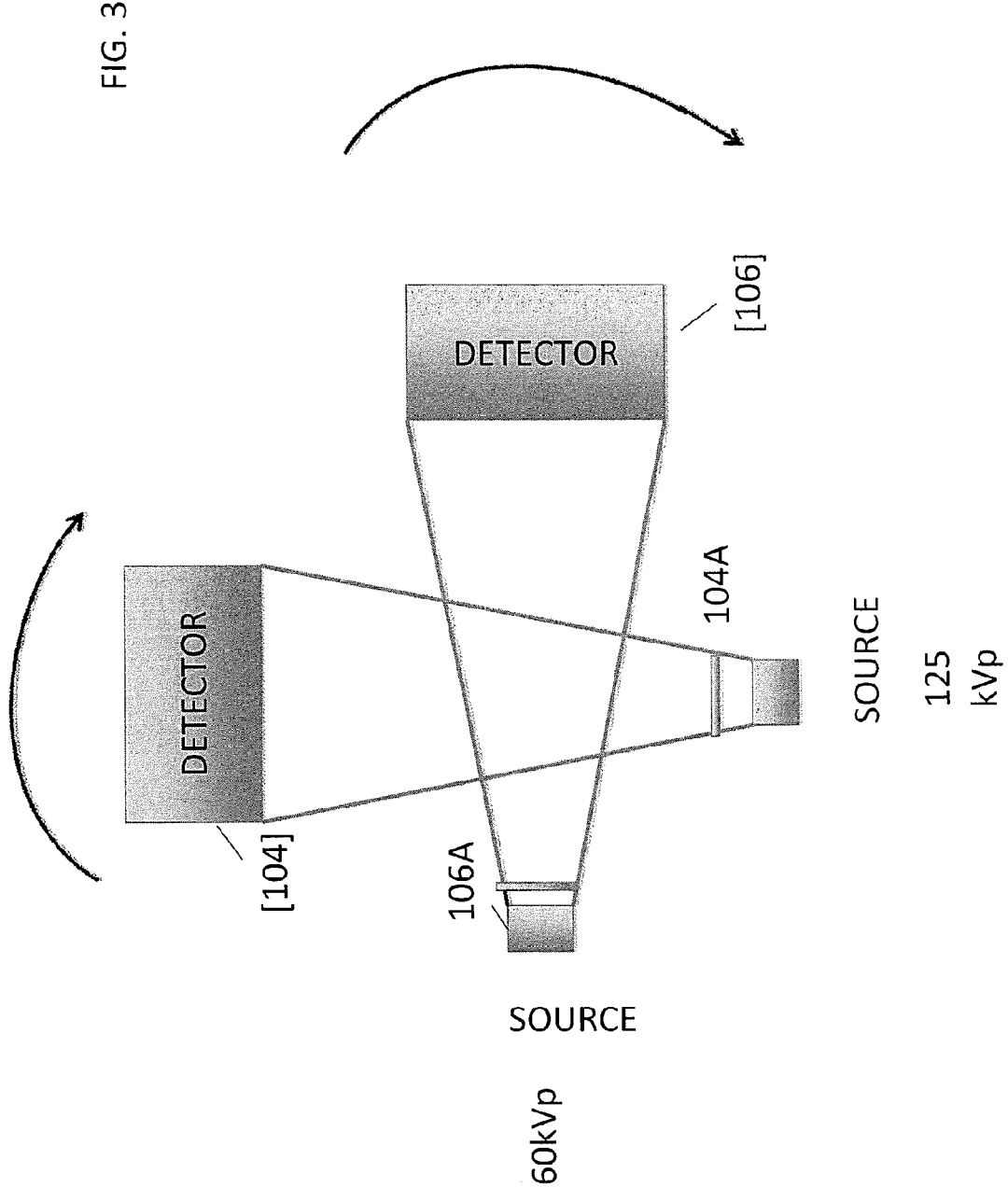
FIG. 3 illustrates an implementation of an imaging technique on a dual C-arm system, with each source operated at a different energy level.

In some embodiments, multiple sources at different energies may be used instead of a single switched source. For example, FIG. 3 shows a bi-plane type imaging system employing two rotating source-detector pairs 104 and 106 each operated at different energies (as shown 60 and 125 kVp). In this configuration, each source may have its own static filters 104A, 106A. In this configuration both systems may be simultaneously rotated and used to record projections at equal times.

Examples of C-Arm and bi-plane imaging systems include Siemens AG Zeego system, which comprises a single source single detector C-ARM apparatus, and a Siemens AG Axiom ARTIS biplane system which has two source detector pairs.

In various time and energy subtraction CT techniques, the differing source energy values (i.e., the x-ray kVp values for the systems shown in FIGS. 2 and 3) may be chosen so as to provide one energy that produces preferential absorption contrast at one energy level, e.g., for a chosen material. For example, in many medical imaging applications, iodine contrast is introduced into the region of interest (e.g., injected into blood vessels). Iodine has an abrupt increase in its x-ray attenuation at 33 keV. Therefore imaging beam kVp values generally in the range of about 50 to 80 kVp are considered appropriate to generate reasonable iodine contrast. In the range of 100 kVp and higher, the iodine contrast is greatly diminished. Accordingly, the high energy range can be greater than about 80 kVp, and the low energy range can be less than about 80 kVp, for example. Subtraction of images obtained with energies in these low and high energy ranges will provide a substantial iodine difference signal. Since soft tissue does not exhibit energy dependence the tissue contrast provided by these two energy ranges is similar so that when a high/low energy subtraction is performed the tissue at least partially cancels out in the subtraction. In some embodiments, a weighting factor is applied to either the high or the low energy images to ensure that tissue cancellation is achieved. In some embodiments, even after this weighting factor is applied, there is still substantial iodine signal left in the subtracted image.

Figure 4:
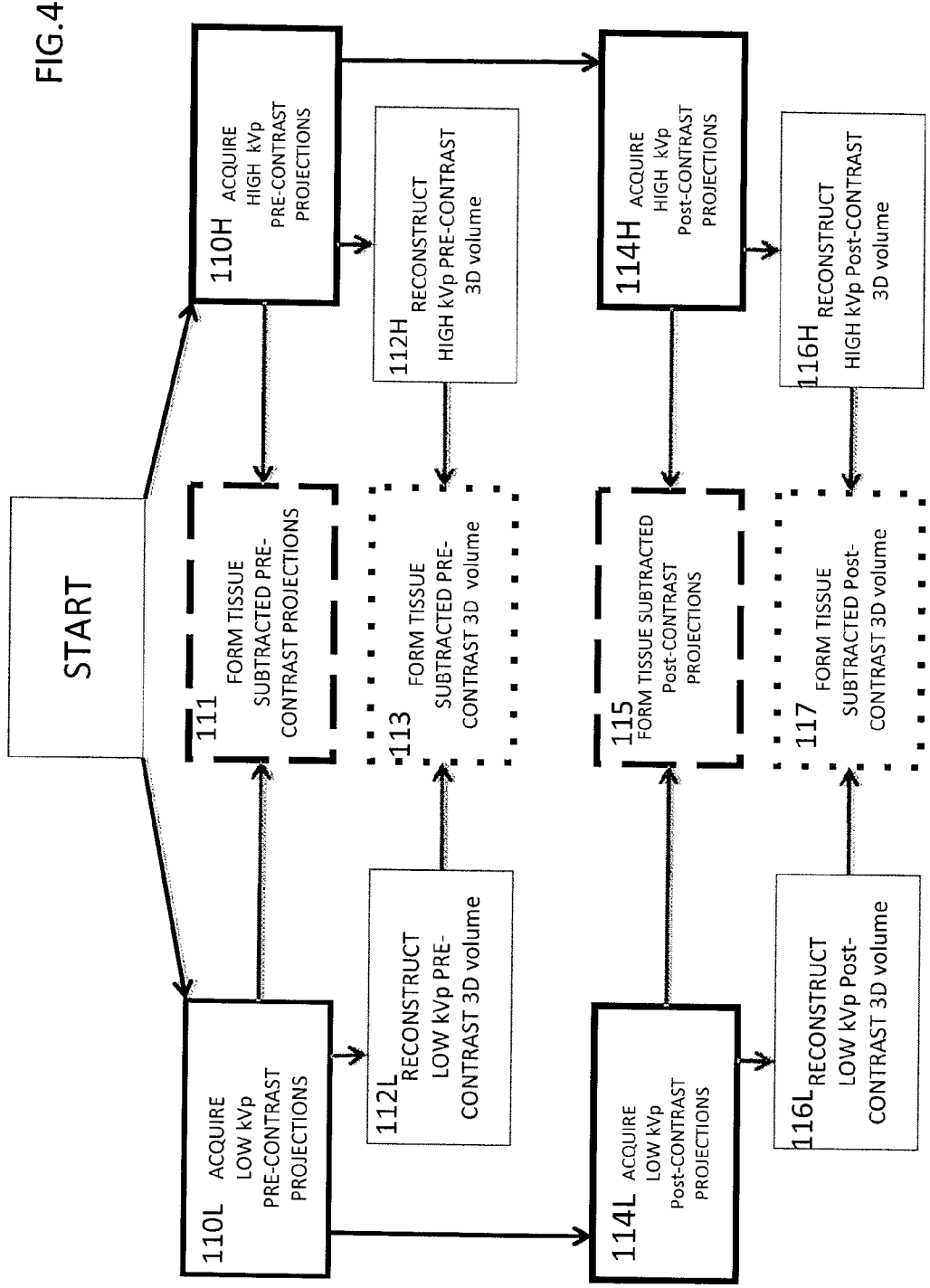
FIG. 4 illustrates steps in a process for forming tissue subtracted pre and post contrast projections and 3D volumes.

FIG. 4 describes an exemplary data acquisition and image reconstruction sequence for a time and energy subtracted CT system of the types described herein. In steps 110L and 110H, Prior to the introduction of a contrast material into the region of interest, pre-contrast low and high energy angular projections are acquired during a sweep of an imaging device (e.g., the apparatus of FIG. 2 or FIG. 3). In step 111, these projections are subtracted, e.g., using a weighted subtraction, to form energy subtracted projections, e.g., with canceled signals from a specific component such as soft tissue (or bone, or iodine).

In steps 112L and 112H, the same high and low energy projections are used to form time independent (i.e., substantially lacking in time resolved information) 3D pre-contrast reconstructions of the 3D volume for each energy. These 3D volumes are subjected to the same subtraction (e.g., weighted subtraction) as used in step 111 for the material selective projections to form a material-selective (usually tissue subtracted) time independent 3D volume representing the selected pre-contrast anatomy 113.

In some embodiments, a subtraction technique of the type described above provides images that are partially or completely insensitive to tissue motion, provided that the energy is switched rapidly enough to give exemplary good registration between the high and low energy exposures. For example, for typical applications, a switchable source (e.g., as shown in FIG. 2) may switch between energies with a period of about 0.1 s or less, about 0.03 s or less, etc., e.g., in the range of 0.02-0.04 s, or 0.1-0.03 s, or any other suitable range.

For some embodiments featuring biplane systems (e.g., as shown in FIG. 3) where each source detector pair provides its own energy, exemplary good registration is maintained over the time required for the gantry to traverse 90 degrees so that matching projections are acquired at each energy. For cardiac applications employing a bi-plane system the use of cardiac gating techniques of the type known in the art may be used to improve tissue registration.

Cardiac gating (also known as cardiac triggering) techniques are techniques in which image acquisition is triggered by a start pulse derived from an electrocardiogram (ECG) taken from the patient during imaging. ECG gating techniques are useful whenever data acquisition is too slow to occur during a short fraction of the cardiac cycle. In some embodiments, and ECG signal is used to produces a trigger signal fed to the control system (e.g., computer 46) of an imaging system to be used as a start signal for data acquisition of the imaging system. The imaging system then automatically acquires data for a time series of images or for a few images at different anatomical levels. Techniques of this type are referred to as prospective ECG gating. Prospective ECG gating can be employed for the bi-plane systems to improve tissue registration.

In some embodiments, retrospective ECG gating may be used. Retrospective ECG gating refers to techniques in which cardiac-gated data are retrospectively assigned to a cardiac cycle phase and hence to the corresponding image.

In some embodiments, tissue subtraction can be performed more effectively by prospective or retrospective ECG gating since the variable positions of the vascular structures and cardiac chambers will vary throughout the cardiac cycle of a particular subject, which can be employed to reduce blurring in the 3D DSA reconstruction resulting from the cardiac and vascular variable positions.

In steps 114L, 114H, 115, 116L, 116H and 117 the above described process are carried out for post-contrast projections acquired with a rotation following contrast injection. These post contrast projections are subjected to an energy subtraction (e.g., a weighted subtraction) to form projections with canceled signals from a specific component such as soft tissue, bone or iodine.

Accordingly, the result of the process is a time resolved series of pre-contrast energy subtracted projections, a pre-contrast energy subtracted time independent 3D volume, a time resolved series of post-contrast energy subtracted projections, and a post-contrast energy subtracted time independent 3D volume. These results may be further processed to provide time and energy subtracted information.

Figure 5:
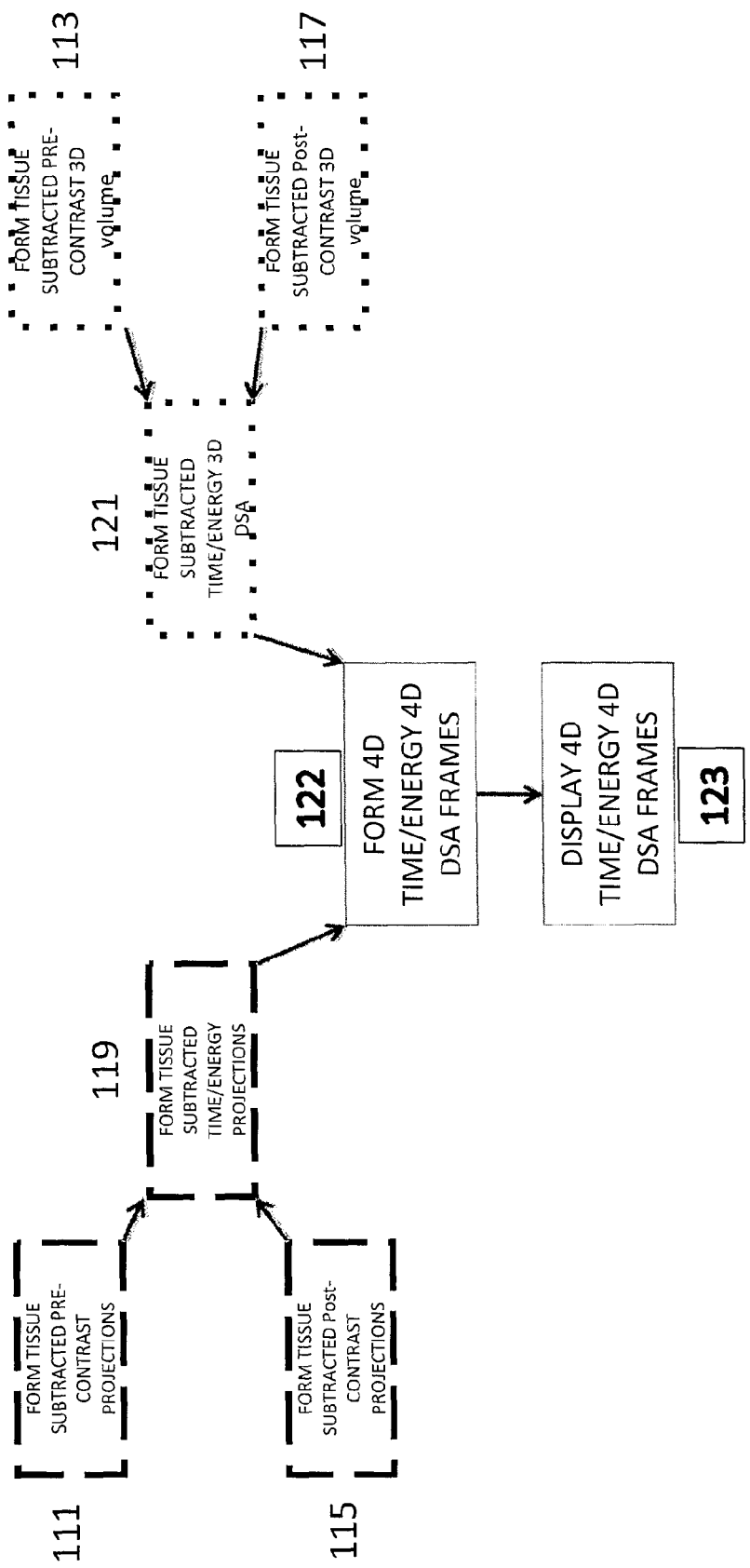
FIG. 5 illustrates steps in a process for forming 4D Energy/Time time frames from projections and 3D volume data.

Referring to FIG. 5, a process is illustrated which uses the results of the process shown in FIG. 4 to generate a time resolved series of 3D reconstructions (referred to as 4D time frames). In step 119, the tissue (i.e., energy) subtracted pre-and post-contrast time resolved projections generated in steps 111 and 115 are subtractively combined to form energy-time subtraction projections (corresponding to second order terms in Equation. 1). In step 121, the pre-and post-contrast tissue (i.e., energy) subtracted time independent 3D volumes generated in steps 113 and 117 are subtractively combined to form (again, second order) energy-time subtracted 3D volume.

Note that the use of two energies as described above provides information to reduce or cancel the signal from one selected material, e.g., tissue or bone. In order to cancel an additional material (e.g., to cancel both bone and tissue) a third energy can be used. In this case the need for time subtraction would be removed. However, in typical applications, this leads to reduced signal to noise ratio relative to the time/energy subtraction method described herein. In the process shown in FIG. 5, the second order energy time subtractions are formed by subtracting a pre-injection tissue subtracted energy subtraction image from a similar image formed after contrast injection. Assuming no bone motion, the bone is subtracted in this process.

In some embodiments, in performing the time subtraction of the pre and post contrast data, it is assumed that bone within a subject has not moved. This is often the case in practice where the primary motion is due to cardiac motion or bowel peristalsis rather than gross patient motion that displaces the bones. In an alternative embodiment, bone movement can be accounted for as well.

In step 122, the energy and time subtracted time dependent series of projection generated in step 119, and the time and energy subtracted time independent 3d volume generated in step 121 are combined to form a time resolved series of time and energy subtracted 3D volumes. As shown, the volumes are DSA volumes, and the series is referred to as a series of "4D" DSA time frames. Note that this time resolved series of 3D volumes corresponds to the third order subtraction term described in Equation 1 representing a time series of 3D tissue subtracted tomographic time frames.

In various embodiments, processing step 122 may include any of the multiplicative projection processing techniques described in any one of SYSTEM AND METHOD FOR FOUR DIMENSIONAL ANGIOGRAPHY AND FLUOROSCOPY, International Patent Application No. PCT/US2010/045637 and TIME RESOLVED DIGITAL SUBTRACTION ANGIOGRAPHY PERFUSION MEASUREMENT METHOD APPARATUS AND SYSTEM, U.S. Provisional Patent Application No. 61/389086 each of which is hereby incorporated by reference in its entirety. For example, SYSTEM AND METHOD FOR FOUR DIMENSIONAL ANGIOGRAPHY AND FLUOROSCOPY, International Patent Application No. PCT/US2010/045637 describes a method in which a time resolved series of 3D volume reconstructions is generated based on a time independent 3D volume and a time resolved series of projections. Each 3D volume in the series is generated by multiplying the time independent volume by a limited number of projections (e.g. two) from the time resolved series of projections. As will be understood by one skilled in the art, this method can readily be adapted for use in processing step 122.

In typical applications (e.g., for visualizing the vasculature of a region of interest), the above described techniques provide suitable results for many DSA applications. However, in some cases (e.g., where it is desirable to image the perfusion bed of a region of interest.) it is advantageous to use the methods described in TIME RESOLVED DIGITAL SUBTRACTION ANGIOGRAPHY PERFUSION MEASUREMENT METHOD APPARATUS AND SYSTEM, U.S. Provisional Patent Application No. 61/389086. These method provide preservation of the signals (e.g., in the tissue perfusion bed) by using a larger number of projections to generate each 3D volume in the time resolved series. In order to maintain adequate temporal resolution, the number of projections used must be less than the usual number that are used for reconstructing time independent 3D vascular volumes. In the case of the CT-like images acquired with a flat detector C-arm angiographic system (as described in detail below), limiting the number of projections can be accomplished by using angular sectors of projections the total temporal duration of which is limited to a clinically acceptable value, typically a fraction of a second (e.g., 1.0 seconds or less, 0.5 seconds or less, 0.25 seconds or less, etc.). For the purpose of generating artifact free, high detail images the use of angular sectors significantly smaller than 180 degrees leads to image artifacts. Accordingly, the techniques described in this reference combine reconstruction (e.g., by filtered back projection) of these limited sectors with reconstruction constraints (e.g. based on a time independent 3D volume created using projection spanning angles of about 180 degrees or more) to reduce the impact of these artifacts on image quality. As will be understood by one skilled in the art, this method can readily be adapted for use in processing step 122.

In step 123, an output is generated based on the time frames generated in step 122. The output may include, for example, sequentially displayed time resolved of the region of interest taken from any arbitrary angle. The images may be displayed using different angles during the temporal evolution using maximum intensity projection (MIP) techniques known in the art.

In some embodiments, parametric images may be formed from the time dependent information in the individual voxels of the 4D volumes. An advantage of the 4D DSA methods of the type described herein is that the time dependence can be analyzed in individual slices in the image volume without the overlap of slice that occurs in conventional DSA. Techniques described herein permit volume region specific analysis of DSA data. As in conventional DSA parametric images such as mean transit time, time to peak opacification, (TTP), maximum achieved intensity (Cmax), and parameters which characterize flow using a combination of these such as the ratio of Cmax to TTP. These capabilities are available using conventional computed tomography systems where rapid gantry rotations provide sufficient time resolution to provide time dependent volume information. Having this capability in a C-arm X-ray interventional suite allows physicians to evaluate interventions without having to transfer patients to a conventional CT suite.

Figure 8:
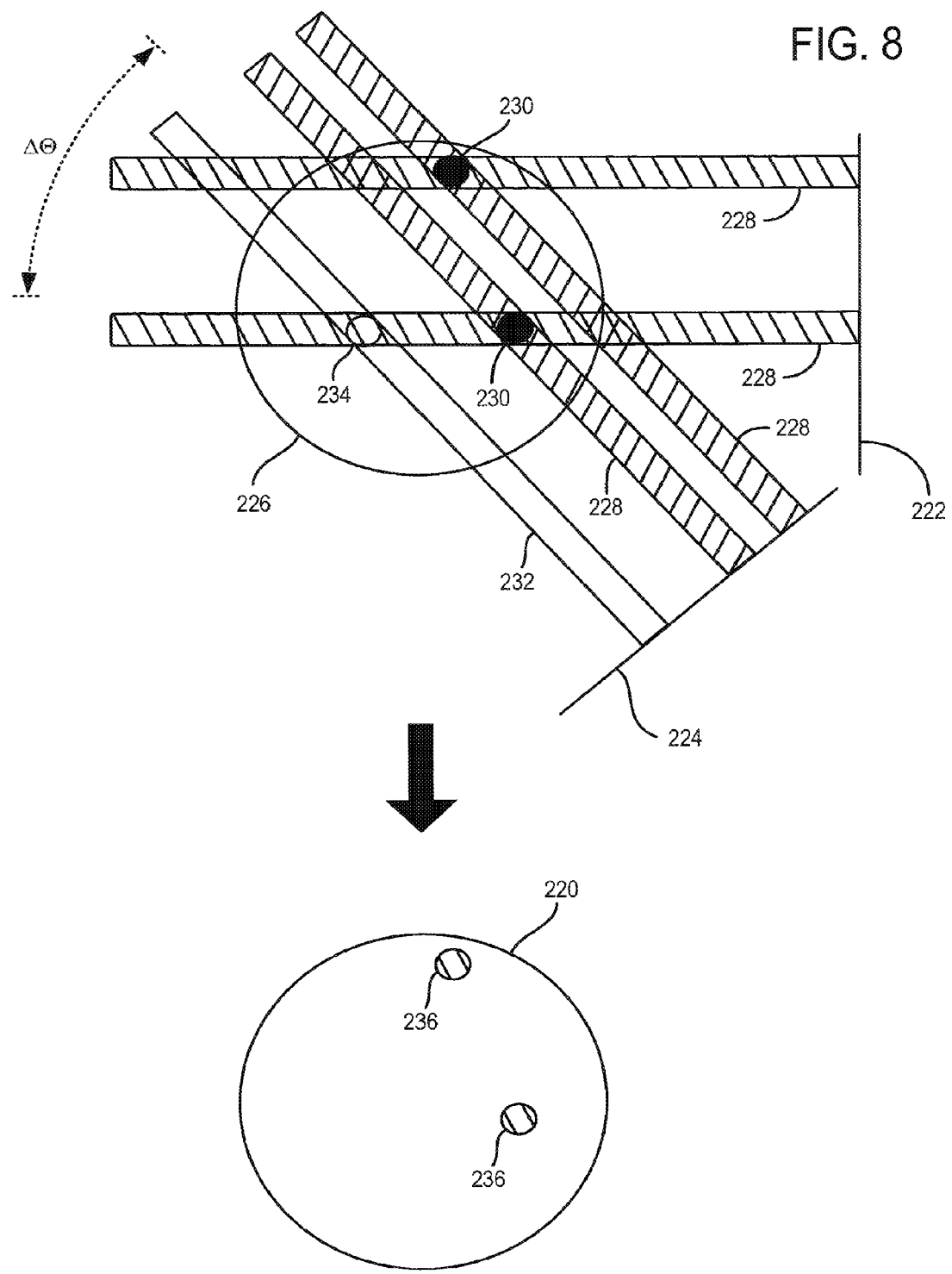
FIG. 8 schematically depicts selective combination of a 3D image generated from a pair of individual projection views selected in accordance with some aspects of the present disclosure.

FIG. 8 schematically depicts one embodiment of a process of combining 2D projection information from two orthogonal angles and a 3D DSA image. Schematically shown is the formation of a 4D-DSA image frame 220 by selectively combining two registered projection images 222 and 224 and a 3D-DSA image without time dependence 226. The formation of the 4D-DSA image frame 220 corresponds to step 122 of FIG. 5. The projection images 222 and 224 can be the energy and time subtracted time dependent series of projection generated in step 119. The 3D-DSA image without time dependence 226 can be the time and energy subtracted time independent 3D volume generated in step 121. Projected arterial signal 228 from the projection images 222 and 224 weights arterial voxels 230 in the 3D-DSA image 226, while the projected signal from pixels without contrast 232 nullifies venous voxels 234 in the 3D-DSA image 226. The resulting 4D-DSA image frame 220, thus, includes weighted arterial signal 236, but does not include undesired venous signals, despite the fact the venous voxels 234 and arterial voxels 230 of the 3D-DSA image are aligned for one of the projection images.

Figure 9:
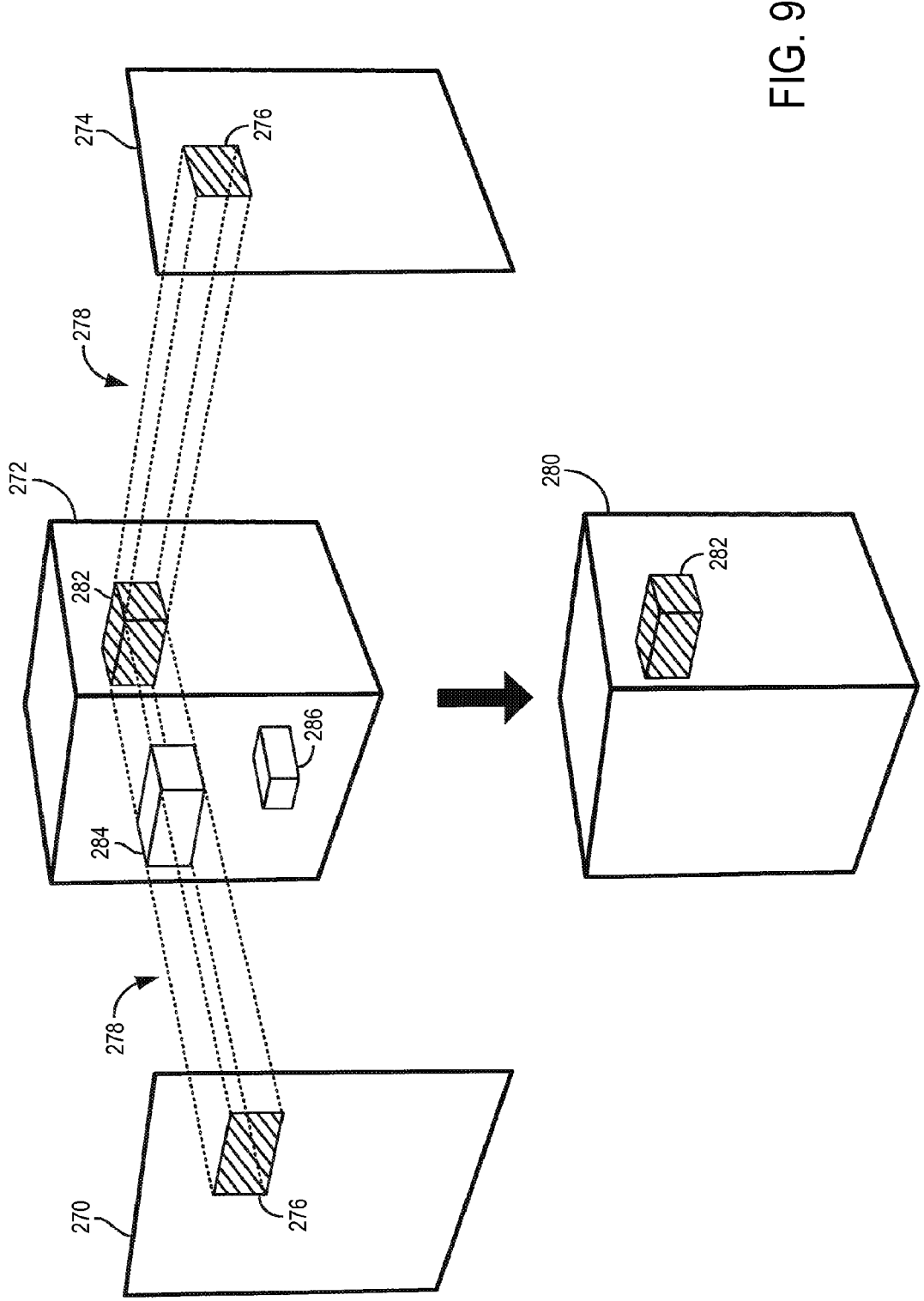
FIG. 9 schematically depicts a multiplication process involving combination of 2D projection information from two orthogonal angles and a 3D DSA image, in accordance with some aspects of the present disclosure.

In FIG. 9, one embodiment of a process of combining 2D projection images and a 3D DSA image is illustrated for the case of bi-plane acquisition. The formation of the 4D-DSA image frame 280 corresponds to step 122 of FIG. 5. The projection images 270 and 274 can be the energy and time subtracted time dependent series of projection generated in step 119. The 3D-DSA image without time dependence 272 can be the time and energy subtracted time independent 3D volume generated in step 121. The projection of arterial signal 276 is indicated generally at 278. The projected values from both of the orthogonal 2D-DSA frames are used to weight the 3D-DSA image and thus produce the 4D-DSA frame 280. Venous signals 284 and 286 are zeroed-out by virtue of being absent in either of the 2D projection images 270 or 274, registered to the 3D-DSA image 272, resulting in the unambiguous isolation of the arterial signal in 282. Again, both the 3D-DSA and orthogonal 2D-DSA images are acquired while a contrast agent is administered to the subject and a signal corresponding to non-vascular structures is removed by subtracting out a mask image.

Figure 6A:
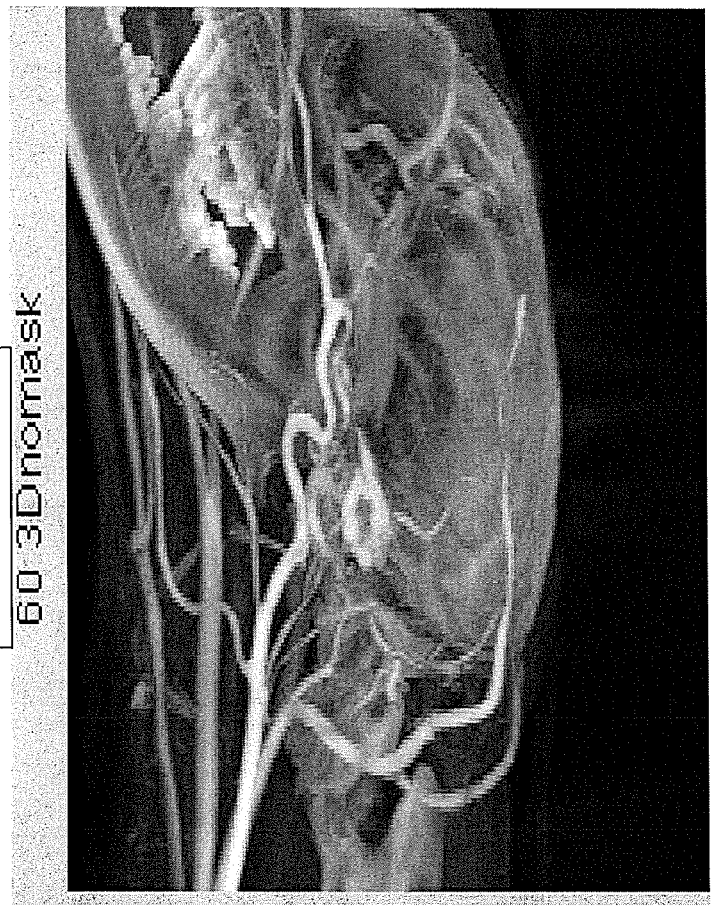
FIG. 6A-6E illustrate representative images corresponding to selected steps illustrated in FIGS. 4 and 5.
Figure 6B:
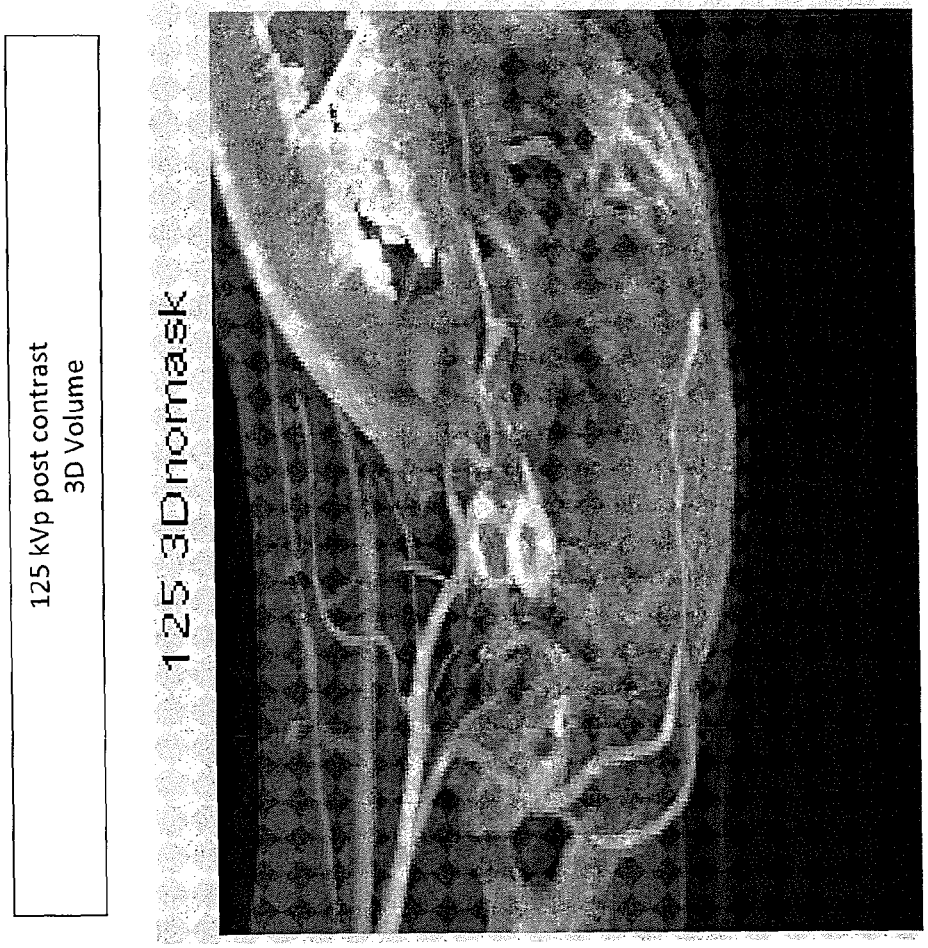
Figure 6C:
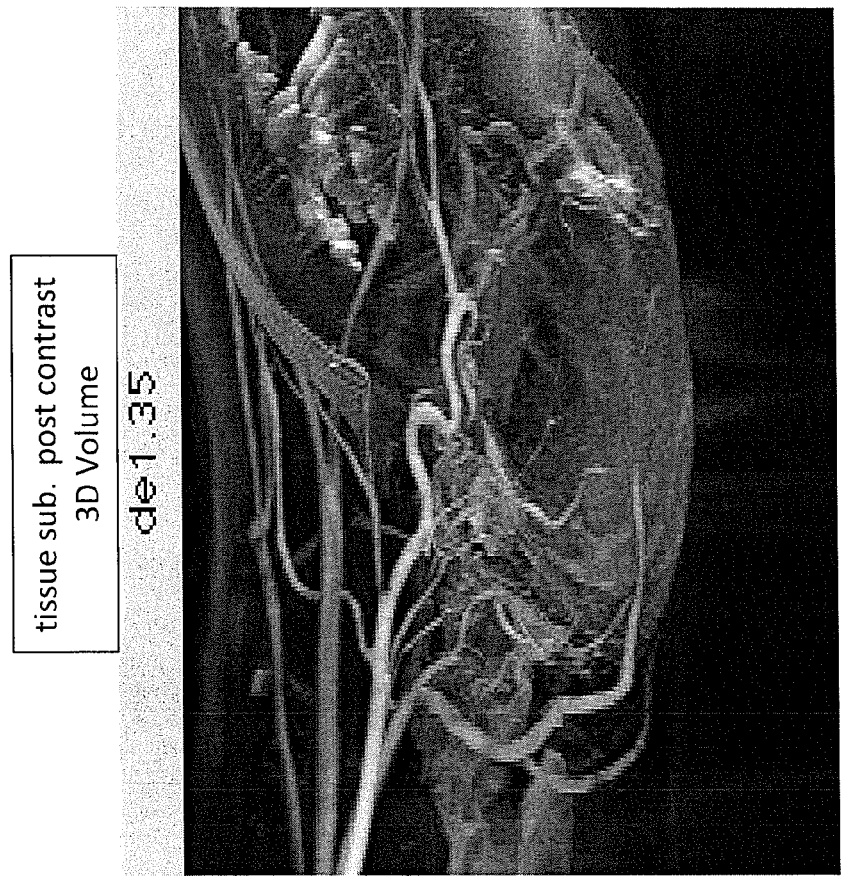
Figure 6D:
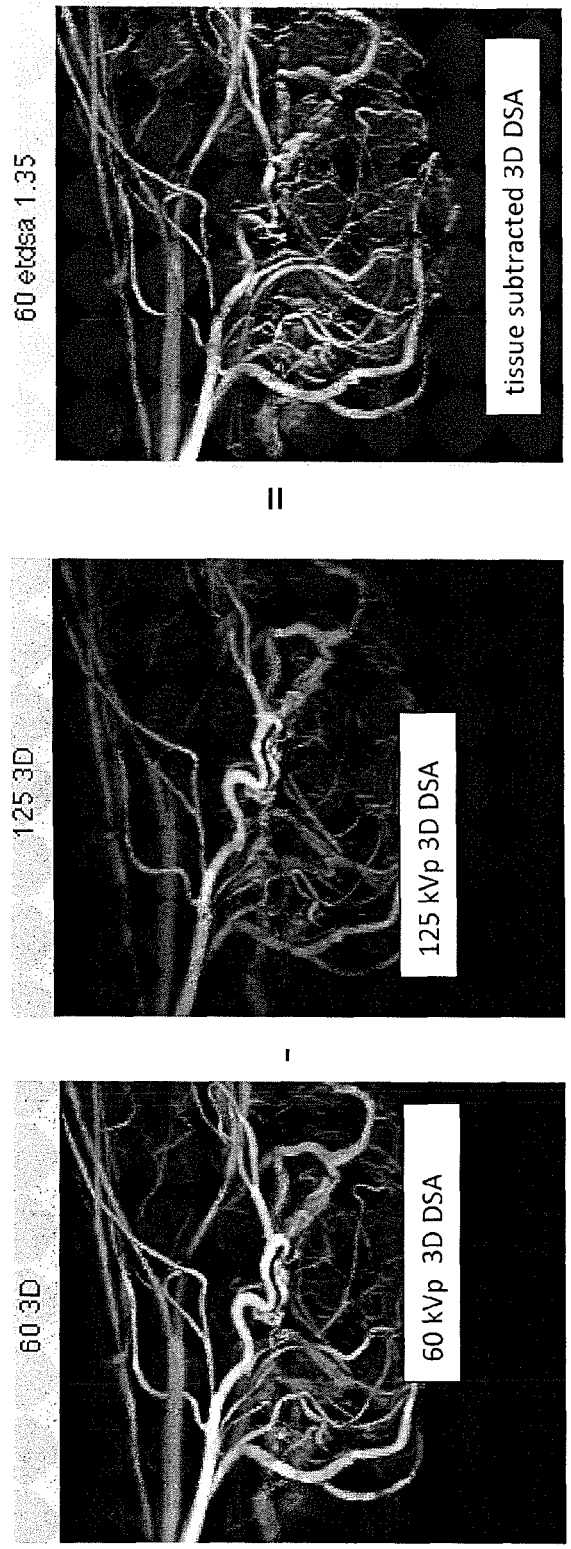

In FIG. 6A-E images corresponding to the processing steps of FIGS. 4 and 5 are shown. FIG. 6A shows an example of the post contrast low energy 3D volume generated in step 116L. FIG. 6B shows an example of the post contrast high energy 3D volume generated in step 116H. FIG. 6C shows the tissue (i.e., energy) subtracted post contrast volume reconstructed generated in step 117. FIG. 6D shows an example of the tissue subtracted 3D DSA volume calculated in step 121.

Figure 6E:
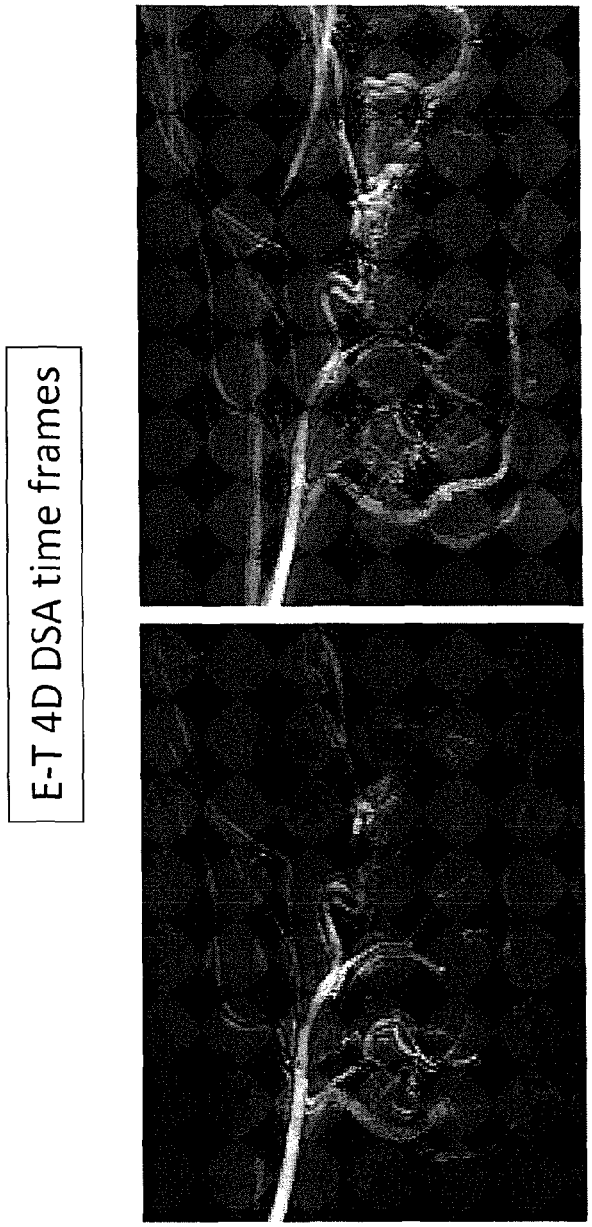
Figure 7:
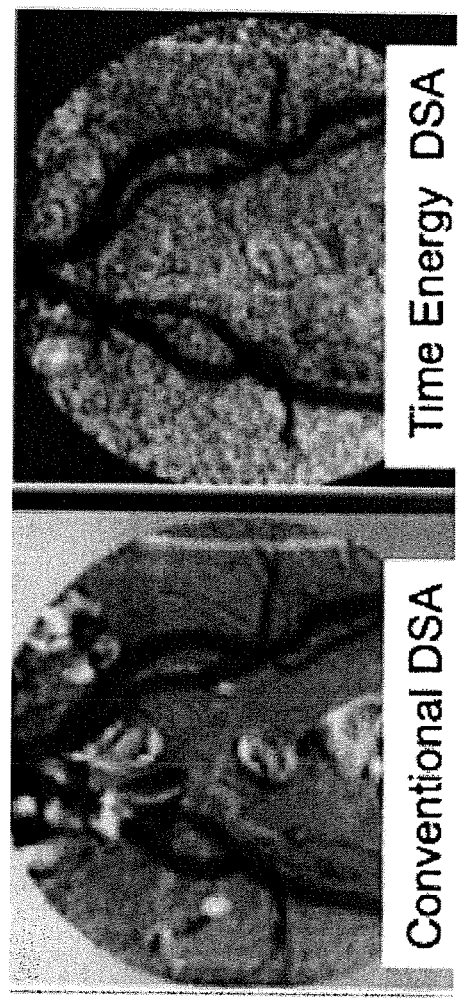
FIG. 7 illustrates a comparison between a conventional 2D DSA image and a time and energy subtracted 2D DSA image.

FIG. 6E shows examples of 2D slices generated based on two of the 4D DSA of the time frames calculated step 122. Note the clarity of the images, clearly showing inflow of contrast into the vasculature. In various embodiments, the result of the techniques described herein is the generation of 4D-DSA time frames that are free of soft tissue motion artifacts and provide fully rotatable 3D volumes displaying injected contrast material in a time series.

The use of time/energy subtraction within the context of the 4D DSA type reconstructions extends the potential of the 4D DSA method to situations in high tissue motion might occur. A primary example is in the abdomen where involuntary bowel peristalsis causes continuous motion. Feasibility studies of the described method have been simulated using non-energy switched systems performing identical scans at two different energies at two different times. These simulations were conducted using 125 and 60 kVp and were done in the head. The tests indicated the size of the difference signals to be expected. Signals were found to be adequate for practical applications.

One or more or any part thereof of the techniques described herein can be implemented in computer hardware or software, or a combination of both. The methods can be implemented in computer programs using standard programming techniques following the method and figures described herein. Program code is applied to input data to perform the functions described herein and generate output information. The output information is applied to one or more output devices such as a display monitor. Each program may be implemented in a high level procedural or object oriented programming language to communicate with a computer system. However, the programs can be implemented in assembly or machine language, if desired. In any case, the language can be a compiled or interpreted language. Moreover, the program can run on dedicated integrated circuits preprogrammed for that purpose.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The computer program can also reside in cache or main memory during program execution. The analysis method can also be implemented as a computer-readable storage medium, configured with a computer program, where the storage medium so configured causes a computer to operate in a specific and predefined manner to perform the functions described herein.

A number of embodiments of the invention have been described. Nevertheless, it will be understood that various modifications may be made without departing from the spirit and scope of the invention.

For example, although in the embodiments described in detail above image projections are received directly from a C-arm system for processing, the images may be received from any other suitable source. For example, the projections may be received (e.g., in real time) from a remote source, e.g., via the internet or outer network. Accordingly, the techniques described herein may be used in telemedical and other such applications. In other embodiments, the projections may be stored, e.g. in database saved on one or more memory devices, and received for processing. Accordingly, the techniques described herein may be used in teaching, simulation, research and other such applications As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above.

Definitions that are contained in text incorporated by reference are excluded to the extent that they contradict definitions in this disclosure.

For the purposes of this disclosure and unless otherwise specified, "a" or "an" means "one or more."

As used herein, the term "comprising" is intended to mean that the compositions and methods include the recited elements, but not excluding others. "Consisting essentially of" when used to define compositions and methods, shall mean excluding other elements of any essential significance to the combination for that intended purpose. "Consisting of" shall mean excluding more than trace elements of other ingredients and substantial method steps for making or using the articles of this disclosure.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of medical imaging using an x-ray imaging device having at least one rotating radiation source and detector pair, comprising:

obtaining a non-contrast low energy time resolved series of image projections of a region of interest in a subject taken at a first energy level in the absence of a contrast agent during a first single rotational acquisition of the imaging device;

obtaining a non-contrast high energy time resolved series of image projections of the region of interest in the subject taken at a second energy level higher than the first energy level in the absence of the contrast agent during the first single rotational acquisition of the imaging device;

obtaining a contrast low energy time resolved series of image projections of the region of interest in the subject taken at the first energy level in the presence of the contrast agent during a second single rotational acquisition of the imaging device;

obtaining a contrast high energy time resolved series of image projections of the region of interest in the subject taken at the second energy level in the presence of the contrast agent during the second single rotational acquisition of the imaging device;

generating a time resolved series of non-contrast energy subtracted image projections based on the non-contrast low energy time resolved series and high energy time resolved series;

generating a time resolved series of contrast energy subtracted image projections based on the contrast low energy time resolved series and high energy time resolved series;

generating a time independent non-contrast energy subtracted three dimensional image based on the non-contrast high energy time resolved series of image projections and the non-contrast low energy time resolved series of image projections;

generating a time independent contrast energy subtracted three dimensional image based on the contrast high energy time resolved series of image projections and the contrast low energy time resolved series of image projections;

generating a time resolved energy-and-time-subtracted series of image projections based on the time resolved series of non-contrast energy subtracted image projections and the time resolved series of contrast energy subtracted image projections;

generating a time independent energy-and-time-subtracted three dimensional image based on the time independent contrast energy subtracted three dimensional image and the time independent non-contrast energy subtracted three dimensional image;

generating a time resolved series of energy-and-time-subtracted three dimensional images including, for each of a plurality of pixels in the time resolved energy-and-time-subtracted series of image projections, projecting the pixel onto the time independent energy-and-time-subtracted three dimensional image along a line passing through the pixel in a direction perpendicular to a plane of an image associated with the pixel, among the time resolved energy-and-time-subtracted series of image projections; and weighting or multiplying a voxel value of the time independent energy-and-time-subtracted three-dimensional image using an attenuation value of the pixel, the voxel value associated with a voxel on which the pixel is projected; and generating an output for display based on the time resolved series of energy-and-time-subtracted three dimensional images.

2. The method of claim 1, wherein the time resolved series of energy-and-time-subtracted three dimensional images comprises a time resolved series of digital subtraction angiography images.

3. The method of claim 1, wherein generating an output for display based on the time resolved series of energy-and-time-subtracted three dimensional images includes displaying at least one image of the subject formed from the time resolved series of energy-and-time-subtracted three dimensional images.

4. The method of claim 3, wherein the at least one image is a parametric image.

5. The method of claim 1, comprising:
obtaining the non-contrast high energy and low energy image projections sequentially; and
obtaining the contrast high energy and low energy image projections sequentially.

6. The method of claim 5, further comprising:
sequentially varying the energy level of the radiation source during each of the first and second rotational acquisitions to obtain the non-contrast high energy and low energy image projections and the contrast high energy and low energy image projections.

7. The method of claim 6, further comprising varying a filtration of the radiation source based on the energy level of the source.

8. The method of claim 1, comprising:
obtaining the non-contrast high energy and low energy image projections simultaneously; and
obtaining the contrast high energy and low energy image projections simultaneously.

9. The method of claim 1, wherein each of the non-contrast low energy time resolved series of image projections, the non-contrast high energy time resolved series of image projections, contrast low energy time resolved series of image projections, and the contrast high energy time resolved series of image projections includes image projections spanning at least 180 degrees.

10. The method of claim 1, wherein the first energy level is less than 80 kVp and the second energy level is greater than 80 kVp.

11. The method of claim 1, wherein the first energy level is in the range of 50 kVp to 80 kVp.

* * * * *